(12) United States Patent
Wiederin

(10) Patent No.: US 10,036,496 B1
(45) Date of Patent: Jul. 31, 2018

(54) FITTING WITH A PROTRUSION

(71) Applicant: Elemental Scientific, Inc., Omaha, NE (US)

(72) Inventor: Daniel R. Wiederin, Omaha, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 0 days.

(21) Appl. No.: 13/655,543

(22) Filed: Oct. 19, 2012

Related U.S. Application Data

(60) Provisional application No. 61/549,324, filed on Oct. 20, 2011.

(51) Int. Cl.
*F16L 25/00* (2006.01)

(52) U.S. Cl.
CPC .................................. *F16L 25/00* (2013.01)

(58) Field of Classification Search
USPC ....... 285/239, 399, 374, 233, 234, 231, 237; 128/200.14, 200.11; 239/338, 346
See application file for complete search history.

(56) References Cited

U.S. PATENT DOCUMENTS

| | | | | |
|---|---|---|---|---|
| 1,051,396 A | * | 1/1913 | Fentress | 285/237 |
| 2,281,633 A | * | 5/1942 | Stitzer | 285/233 |
| 2,396,204 A | * | 3/1946 | Robinson | 239/338 |
| 3,331,621 A | * | 7/1967 | Bagnulo | 285/374 |
| 3,667,785 A | * | 6/1972 | Kapeker | 285/231 |
| 3,916,502 A | * | 11/1975 | Bagnulo | 285/374 |
| 4,521,038 A | * | 6/1985 | Cerny | 128/205.13 |
| 5,884,846 A | * | 3/1999 | Tan | 239/346 |
| 6,712,098 B2 | * | 3/2004 | Sakazaki et al. | 285/231 |
| 6,859,272 B2 | * | 2/2005 | Rutzke et al. | 239/423 |
| 7,121,590 B1 | * | 10/2006 | Alveby | F16L 35/00 285/239 |
| 8,156,933 B2 | * | 4/2012 | Raghuprasad | 128/200.14 |
| 8,439,030 B2 | * | 5/2013 | King | 128/200.14 |
| 2006/0006643 A1 | * | 1/2006 | Schultz | 285/239 |

* cited by examiner

*Primary Examiner* — David Bochna
(74) *Attorney, Agent, or Firm* — Advent, LLP; Kevin E. West

(57) ABSTRACT

A connector is described that comprises a connector body with a connector end extending longitudinally from the connector body. The connector end comprises a generally cylindrical outer surface and a generally cylindrical inner surface. The generally cylindrical outer surface has a protrusion (e.g., a bulbous protrusion) providing a thickened cross-sectional area in the region of the connector end proximate to the protrusion so that the connector end can be connected to a second connector by inserting the second connector into the connector end. The second connector can also comprise a bulbous protrusion, and may be a nebulizer. A tube can be connected to the connector body (e.g., using a threaded connector).

17 Claims, 7 Drawing Sheets

FITTING WITH A PROTRUSION

CROSS-REFERENCE TO RELATED APPLICATIONS

The present application claims the benefit under 35 U.S.C. § 119(e) of U.S. Provisional Application Ser. No. 61/549,324, filed Oct. 20, 2011, and titled "FITTING WITH A PROTRUSION," which is herein incorporated by reference in its entirety.

BACKGROUND

Plastic tubing is often connected to laboratory equipment by sliding the tubing over a protruding section of a generally cylindrical connecting portion of the equipment. For example, a connector can have an end formed in the shape of a truncated cone, with the smaller diameter end of the truncated cone proximal to the end of the connector and the larger diameter end of the cone distal to the end of the connector. In this manner, the tubing can be slid onto the connector over the cone. The increasing diameter of the cone encountered by the tubing allows the tubing to gradually expand as it covers the connector, while providing resistance to movement of the tube in the opposite direction.

SUMMARY

A connector is described that comprises a connector body with a connector end extending longitudinally from the connector body. The connector end comprises a generally cylindrical outer surface and a generally cylindrical inner surface. The generally cylindrical outer surface has a protrusion (e.g., a bulbous protrusion) providing a thickened cross-sectional area in the region of the connector end proximate to the protrusion so that the connector end can be connected to a second connector by inserting the second connector into the connector end. The second connector can also comprise a bulbous protrusion, and may be a nebulizer. A tube can be connected to the connector body (e.g., using a threaded connector).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIGS. 1A and 1B are a cross-sectional side elevation view illustrating a fitting for connecting to a nebulizer in a partially inserted state (FIG. 1A) and a fully inserted state (FIG. 1B), where the fitting includes a first end having a generally cylindrical outer surface and a generally cylindrical inner surface, where the generally cylindrical outer surface has a protrusion providing a thickened cross-sectional area in the region of the first end proximate to the protrusion in accordance with an example implementation of the present disclosure.

FIG. 2 is a cross-sectional side elevation view of the fitting illustrated in FIG. 1.

FIG. 3 is a side elevation view illustrating a fitting including a first end having a generally cylindrical outer surface and a generally cylindrical inner surface, where the generally cylindrical outer surface has a protrusion providing a thickened cross-sectional area in the region of the first end proximate to the protrusion in accordance with an example implementation of the present disclosure.

DETAILED DESCRIPTION

Overview

Plastic tubing is often connected to laboratory equipment by sliding the tubing over a protruding section of a generally cylindrical connecting portion of the equipment. For example, a connector can have an end formed in the shape of a truncated cone, with the smaller diameter end of the truncated cone proximal to the end of the connector and the larger diameter end of the cone distal to the end of the connector. In this manner, the tubing can be slid onto the connector over the cone. The increasing diameter of the cone encountered by the tubing allows the tubing to gradually expand as it covers the connector, while providing resistance to movement of the tube in the opposite direction. In this manner, the connector is designed to retain the tubing and prevent it from sliding off the connector. Thus, when removal of the tubing is desired, the tubing must typically be cut away from the connector. This may require additional effort on the part of a laboratory technician, as well as creating material waste as sections of a tube are cut away each time the tube is used in the laboratory.

Accordingly, the present disclosure is directed to a fitting for connecting to a connector having a protrusion, where the fitting may be easily connected to and disconnected from the connector. The fitting may include a connector body having a first end and a second end. The first end may extend longitudinally from the connector body. The first end may have a generally cylindrical outer surface and a generally cylindrical inner surface. The generally cylindrical outer surface may have a protrusion providing a thickened cross-sectional area in the region of the first end proximate to the protrusion, so that the first end can be connected to a connector having another protrusion by inserting the connector into the first end of the connector body such that the first end of the connector body flexes to removably secure the connector. In this manner, the fitting may provide a snap-on, quick-connect connection that can provide a seal between the fitting and the connector, while still allowing the first end of the fitting to be separated from the connector by pulling the components apart. In implementations, the connector (or an end of the connector) may be formed from a material such as Polyvinylidene Fluoride (PVDF), Perfluoroalkoxy (PFA), or another flexible material, semi-flexible material, semi-rigid material, and so forth.

Example Implementations

Figure 1A:
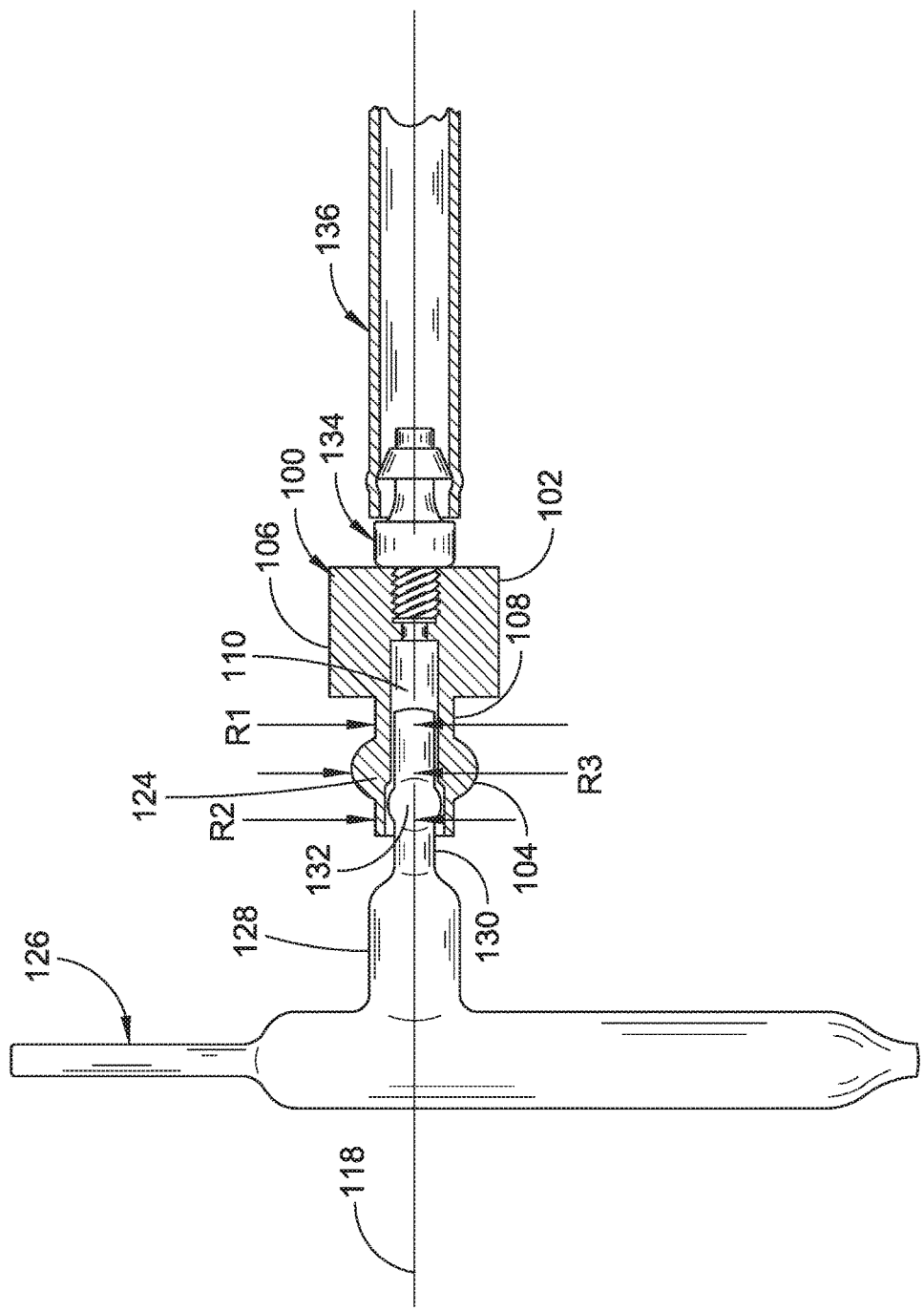
Figure 1B:
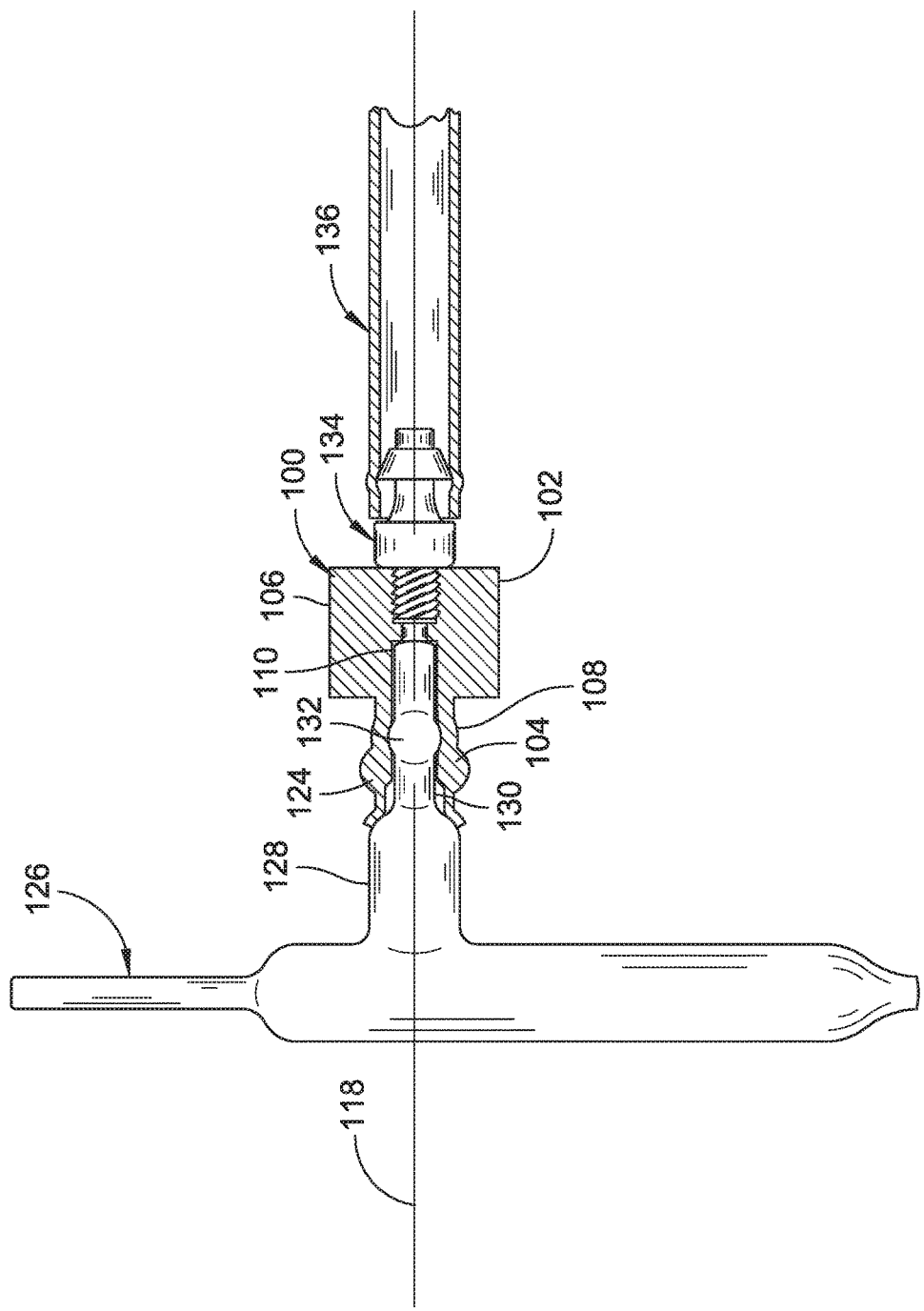
Figure 2:
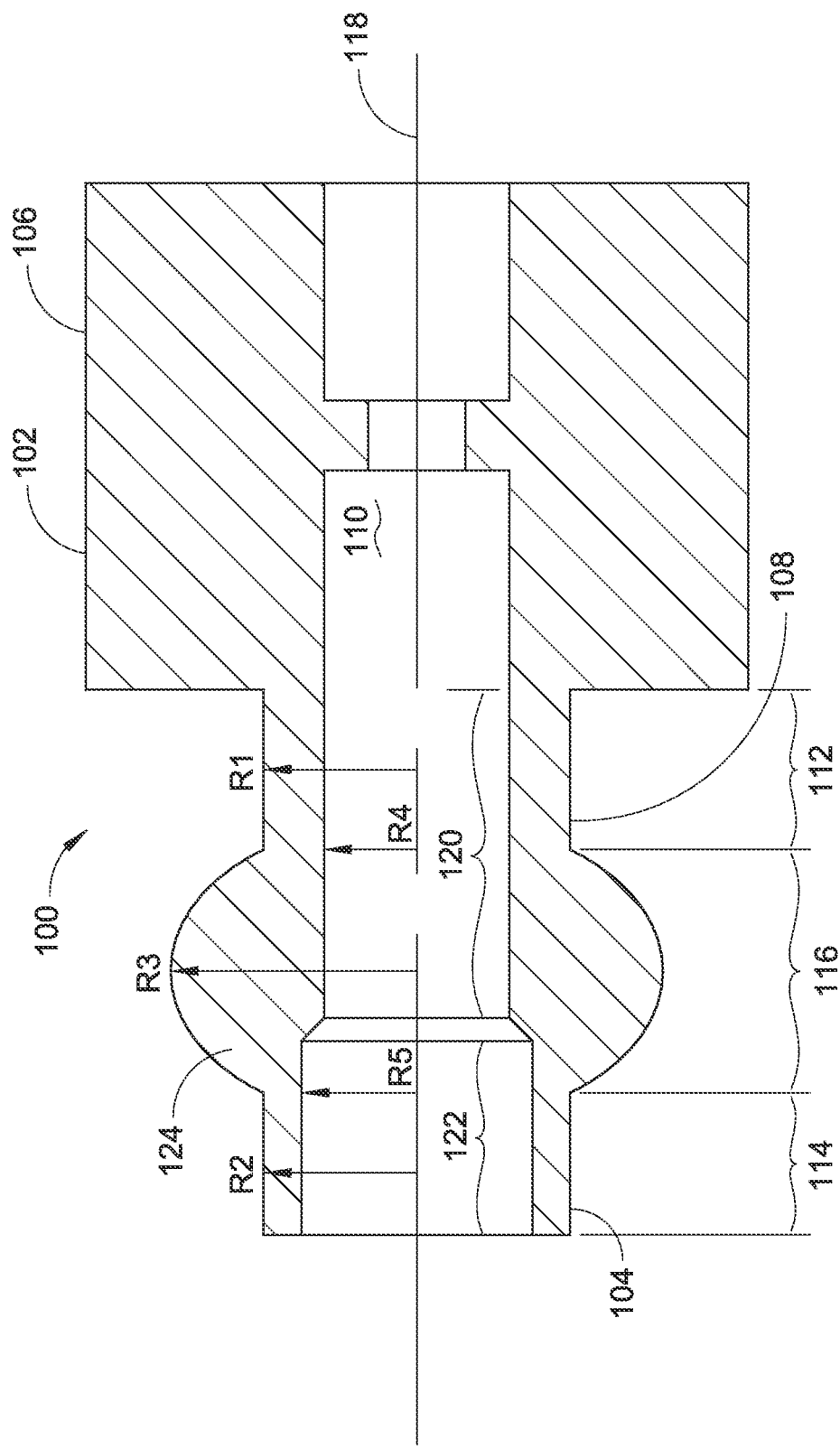
Figure 3:
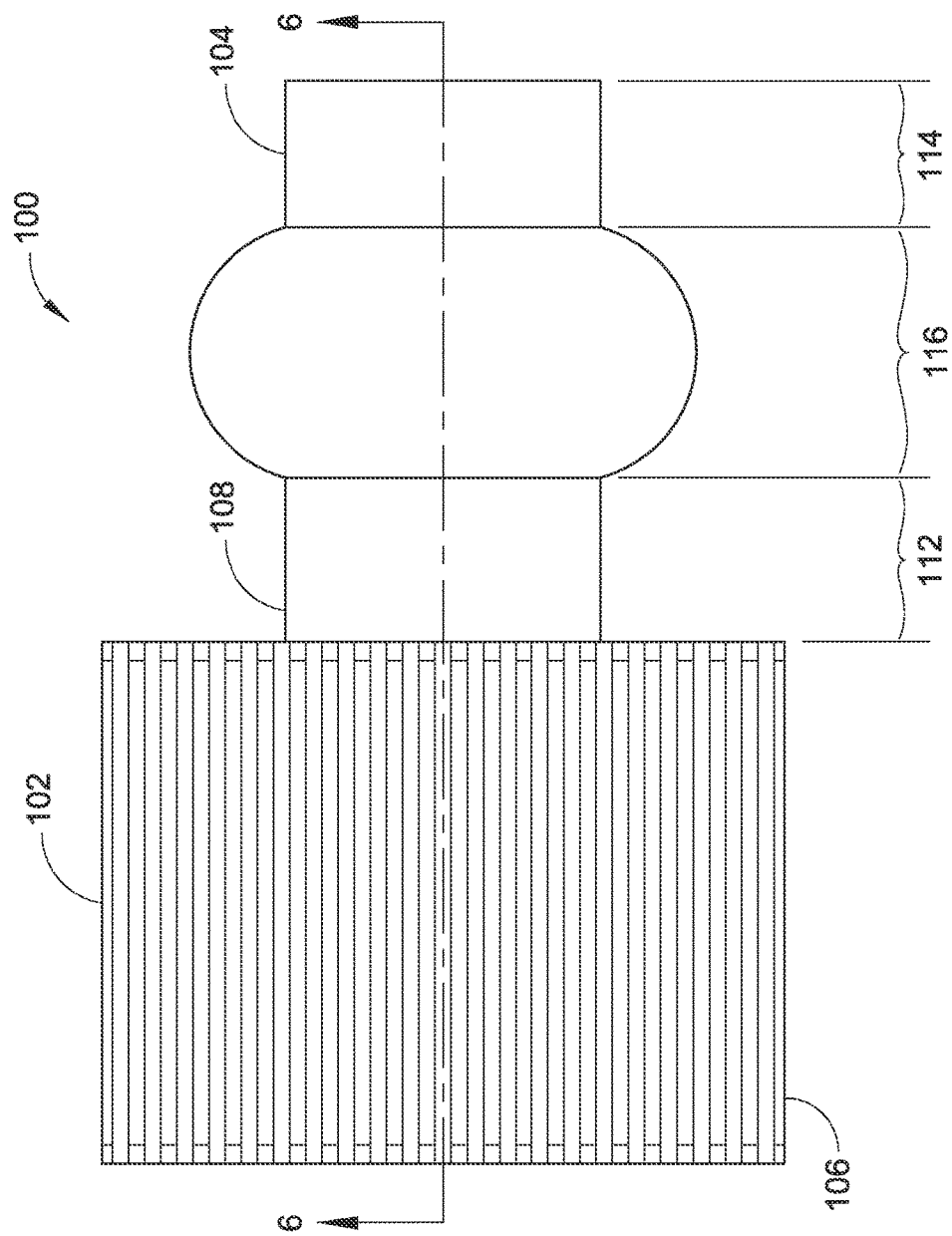
Figure 4:
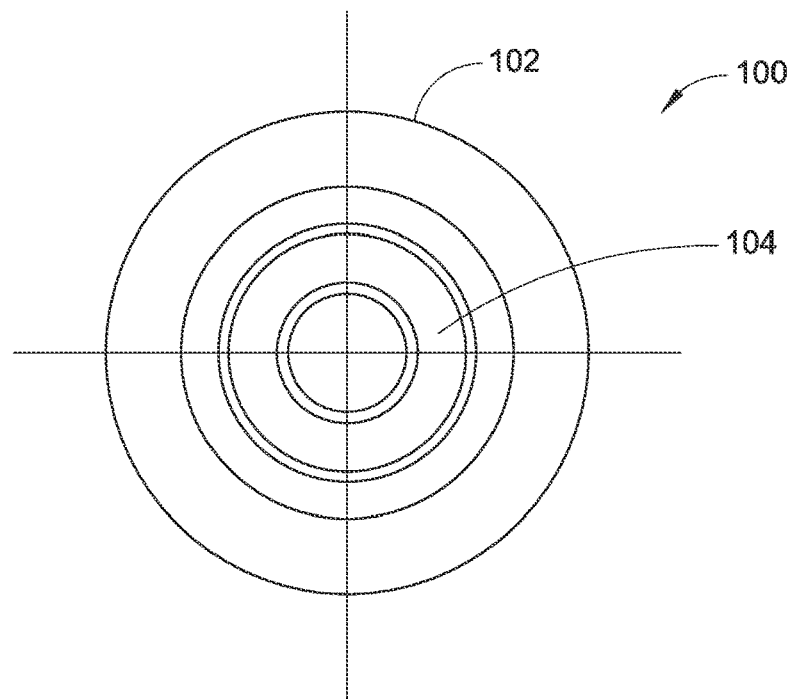
FIG. 4 is an end elevation view of the fitting illustrated in FIG. 3.
Figure 5:
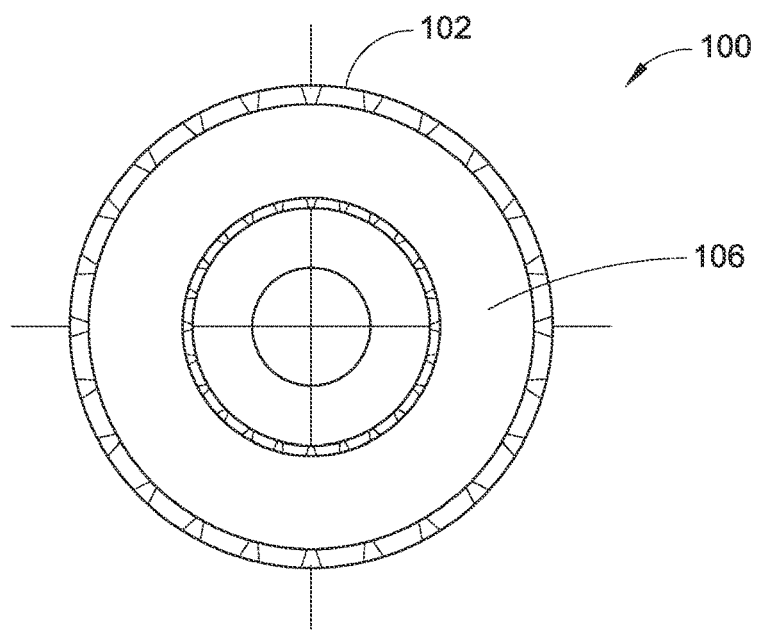
FIG. 5 is another end elevation view of the fitting illustrated in FIG. 3.
Figure 6:
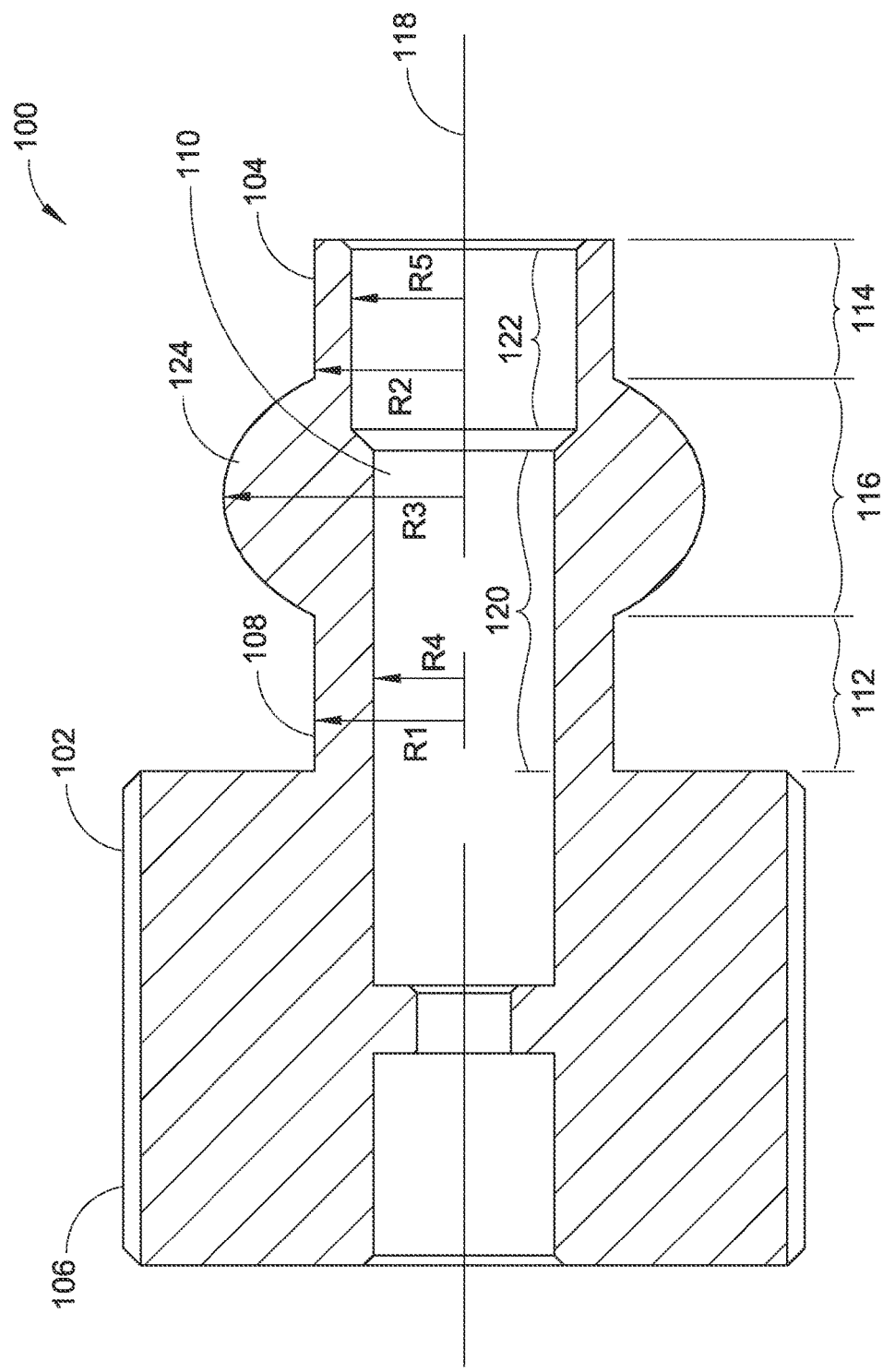
FIG. 6 is a cross-sectional side elevation view of the fitting illustrated in FIG. 3.
Figure 7:
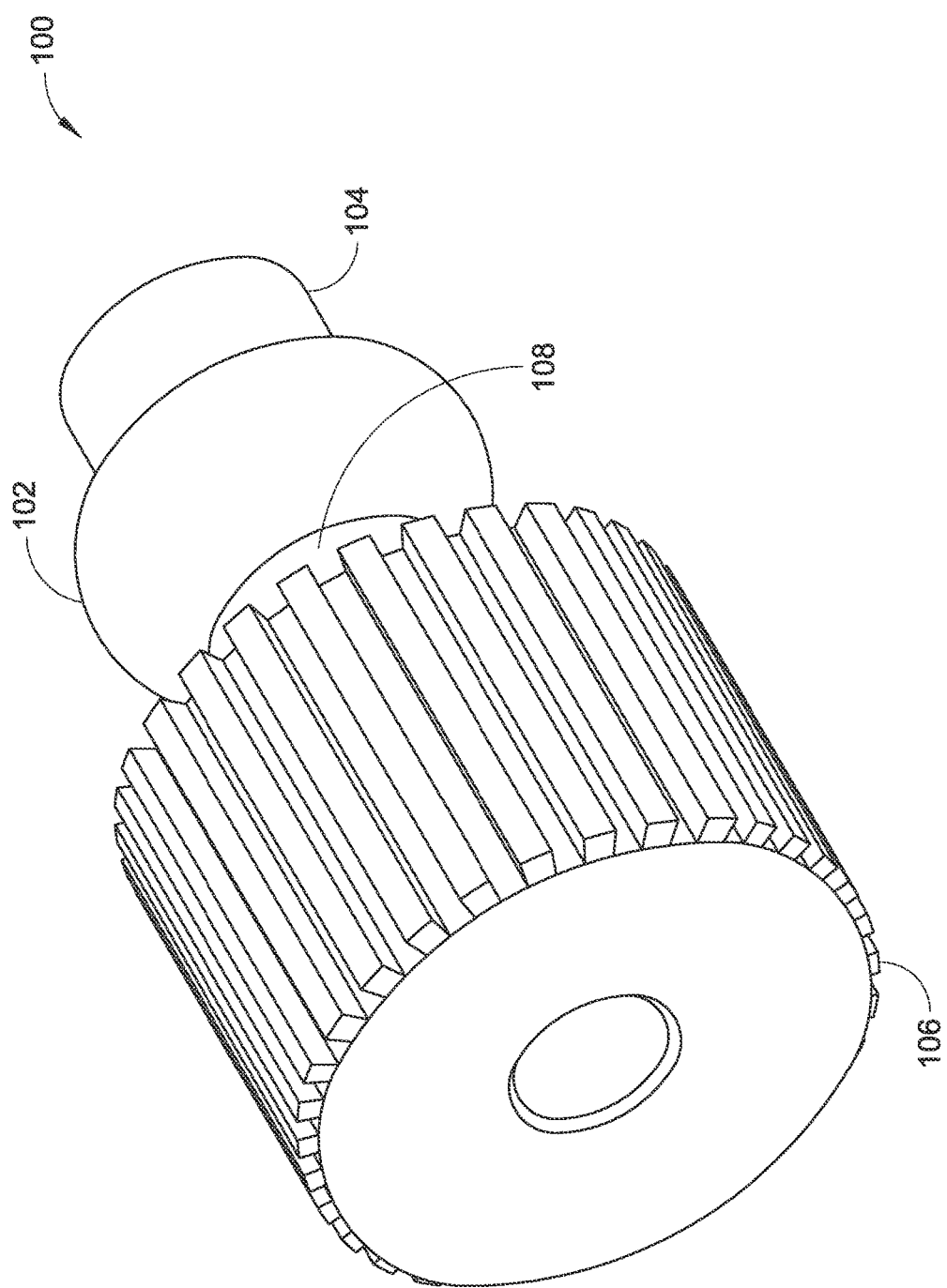
FIG. 7 is a perspective view of the fitting illustrated in FIG. 3.

FIGS. 1 through 7 illustrate fittings in accordance with example implementations of the present disclosure. As shown, a fitting 100 includes a connector body 102 having a first end (connector end) 104 and a second end 106. The first end 104 extends longitudinally from the connector body 102, and includes a generally cylindrical outer surface 108 and a generally cylindrical inner surface 110. The generally cylindrical outer surface 108 has a protrusion along the first end 104 of the connector body 102. For example, the first end 104 of the connector body 102 may have a first cylindrical outer surface segment 112, a second cylindrical outer surface segment 114, and a bulbous protrusion 116 positioned between the first cylindrical outer surface segment 112 and the second cylindrical outer surface segment 114.

The bulbous protrusion 116 has a larger diameter than the diameter of the first cylindrical outer surface segment 112 and the diameter of the second cylindrical outer surface segment 114. For instance, the first cylindrical outer surface segment 112 may have a radius R1 extending from a longitudinal axis 118 of the first end 104, the second cylindrical outer surface segment 114 may have a radius R2 extending from the longitudinal axis 118, and the bulbous protrusion 116 may have a radius R3 extending from the longitudinal axis 118. The radius R1 of the first cylindrical outer surface segment 112 and the radius R2 of the second cylindrical outer surface segment 114 may be less than the radius R3 of the bulbous protrusion 116.

The larger radius R3 of the bulbous protrusion 116 is configured to provide a thickened cross-sectional area for the first end 104 of the connector body 102 in the region of the protrusion. For example, the first end 104 of the connector body 102 may have a first cylindrical inner surface segment 120 and a second cylindrical inner surface segment 122, which form the generally cylindrical inner surface 110. The first cylindrical inner surface segment 120 may have a radius R4 and the second cylindrical inner surface segment 122 may have a radius R5. The amount of material between the generally cylindrical inner surface 110 and the generally cylindrical outer surface 108 in the region of the bulbous protrusion 116 (e.g., between radius R3 and radii R4, R5) may be more than the amount of material in the regions of the first cylindrical outer surface segment 112 and the second cylindrical outer surface segment 114 (e.g., between radius R1 and radius R4 and between radius R2 and radius R5).

Thus, the bulbous protrusion 116 provides a thickened cross-sectional area 124 in the region of the first end 104 proximate to the bulbous protrusion 116 so that the first end 104 can be connected to a connector having another protrusion. For example, the first end 104 of the connector body 102 can be connected to a nebulizer 126 using a connector 128 having a generally cylindrical outer surface 130 with a bulbous protrusion 132 by inserting connector 126 into first end 104 of the connector body 102 (shown partially inserted in FIG. 1A). When the connector 128 is fully inserted (FIG. 1B) into the first end 104 of the connector body 102, the bulbous protrusion 132 is configured to extend between the bulbous protrusion 116 and the second end 106 of the connector body 102 such that the first end 104 of the connector body 102 flexes to removably secure the connector 128. In this manner, the fitting 100 may provide a snap-on, quick-connect connection between the fitting 100 and the connector 128, while still allowing the first end 104 of the fitting 100 to be separated from the connector 128 by pulling the components 100, 128 apart.

In implementations, the second end 106 of the connector body 102 may be threaded to receive a connector, such as a threaded connector 134 inserted into the second end 106. Further, the threaded connector 134 may be connected to a tube, such as a flexible tube 136. Also, it should be noted that the connector body 102 and the threaded connector 134 may be of unitary construction and/or may be formed together, such as co-molded, and so forth.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A connector comprising:
    a connector body; and
    a connector end extending longitudinally from the connector body, the connector end comprising a generally cylindrical outer surface and a generally cylindrical inner surface, the generally cylindrical outer surface having a protrusion providing a thickened cross-sectional area in the region of the connector end proximate to the protrusion so that the connector end can be connected to a second connector by inserting the second connector into the connector end, the region of the connector end proximate to the protrusion including a generally cylindrical inner surface segment wherein the connector end is flexible to removably secure the connector to the second connector, and wherein a second end of the connector body comprises threads configured to connect to a threaded connector.

2. The connector as recited in claim 1, wherein the protrusion comprises a bulbous protrusion.

3. The connector as recited in claim 1, wherein the protrusion is positioned between a first cylindrical outer surface segment and a second cylindrical outer surface segment of the connector end.

4. The connector as recited in claim 1, wherein the second connector comprises a second protrusion disposed of an end of the second connector, the second protrusion configured to extend between the protrusion and a second end of the connector body when the connector is connected to the second connector.

5. The connector as recited in claim 1, wherein the second connector comprises a nebulizer.

6. The connector as recited in claim 1, wherein the threaded connector is connected to a tube.

7. A system comprising:
    a connector body;
    a connector end extending longitudinally from the connector body, the connector end comprising a generally cylindrical outer surface and a generally cylindrical inner surface, the generally cylindrical outer surface having a protrusion providing a thickened cross-sectional area in the region of the connector end proximate to the protrusion so that the connector end can be connected to a second connector by inserting the second connector into the connector end, the region of the connector end proximate to the protrusion including a generally cylindrical inner surface segment wherein the connector end is flexible to removably secure the connector to the second connector; and
    a tube connected to the connector body, wherein a second end of the connector body comprises threads configured to connect to a threaded connector for connecting the tube to the connector body.

8. The connector as recited in claim 7, wherein the protrusion comprises a bulbous protrusion.

9. The connector as recited in claim 7, wherein the protrusion is positioned between a first cylindrical outer surface segment and a second cylindrical outer surface segment of the connector end.

10. The connector as recited in claim 7, wherein the second connector comprises a second protrusion disposed of an end of the second connector, the second protrusion configured to extend between the protrusion and a second end of the connector body when the connector is connected to the second connector.

11. The connector as recited in claim 7, wherein the second connector comprises a nebulizer.

12. A system comprising:
   a first connector comprising a connector body having a first end and a second end;
   a second connector configured to connect to the first connector, the second connector comprising a bulbous protrusion; and
   a connector end extending longitudinally from the second end of the connector body, the connector end comprising a generally cylindrical outer surface and a generally cylindrical inner surface, the generally cylindrical outer surface having a protrusion providing a thickened cross-sectional area in the region of the connector end proximate to the protrusion so that the connector end can be connected to the second connector by inserting the second connector into the connector end so that the bulbous protrusion of the second connector is disposed longitudinally past the protrusion and between the protrusion and the second end of the first connector, the region of the connector end proximate to the protrusion including a generally cylindrical inner surface segment, the protrusion being bulbous in shape.

13. The connector as recited in claim 12, wherein the protrusion comprises a bulbous protrusion.

14. The connector as recited in claim 12, wherein the protrusion is positioned between a first cylindrical outer surface segment and a second cylindrical outer surface segment of the connector end.

15. The connector as recited in claim 12, wherein the second connector comprises a nebulizer.

16. The connector as recited in claim 12, wherein the second end of the connector body comprises threads configured to connect to a threaded connector.

17. The connector as recited in claim 16, wherein the threaded connector is connected to a tube.

* * * * *